(12) United States Patent
Wang et al.

(10) Patent No.: US 9,265,752 B2
(45) Date of Patent: Feb. 23, 2016

(54) TRANSDERMAL PATCH CONTAINING ROTIGOTINE

(75) Inventors: Shuming Wang, Beijing (CN); Huiyong Xue, Beijing (CN); Li Wang, Beijing (CN); Enhong Zhang, Beijing (CN); Hongjun Lian, Beijing (CN); Xiaoyan Shi, Beijing (CN); Guohua Chi, Beijing (CN); Yucheng Lu, Beijing (CN); Xiquan Liu, Beijing (CN); Li Song, Beijing (CN); Xuying Zhong, Beijing (CN); Hongguang Du, Beijing (CN)

(73) Assignee: Jiangsu Kangbeide Pharmaceuticals Co. Ltd., Nanjing (CN)

( * ) Notice: Subject to any disclaimer, the term of this patent is extended or adjusted under 35 U.S.C. 154(b) by 461 days.

(21) Appl. No.: 12/667,915

(22) PCT Filed: Jul. 3, 2008

(86) PCT No.: PCT/CN2008/001267
§ 371 (c)(1),
(2), (4) Date: Jun. 14, 2010

(87) PCT Pub. No.: WO2009/006787
PCT Pub. Date: Jan. 15, 2009

(65) Prior Publication Data
US 2011/0027345 A1 Feb. 3, 2011

(30) Foreign Application Priority Data
Jul. 6, 2007 (CN) .......................... 2007 1 0118491

(51) Int. Cl.
| | |
|---|---|
| A61K 9/70 | (2006.01) |
| A61K 31/381 | (2006.01) |
| A61P 25/16 | (2006.01) |

(52) U.S. Cl.
CPC ............ *A61K 31/381* (2013.01); *A61K 9/7053* (2013.01); *A61K 9/7061* (2013.01); *A61K 9/7069* (2013.01)

(58) Field of Classification Search
None
See application file for complete search history.

(56) References Cited

U.S. PATENT DOCUMENTS 5,474,783 A * 12/1995 Miranda et al. ............... 424/448
6,884,434 B1    4/2005 Muller et al.
(Continued)

FOREIGN PATENT DOCUMENTS

| CN | 1295470   | 5/2001 |
|---|---|---|
| CN | 1640500 A | 7/2005 |

(Continued)

OTHER PUBLICATIONS

Bartholomew, E. et al. Acrylic Pressure Sensitive Adhesives Exhibiting Enhanced Adhesion to Low Surface Energy Substrates (2015), Avery Dennison Performance Adhesive Center.*

(Continued)

*Primary Examiner* — Kevin S Orwig
(74) *Attorney, Agent, or Firm* — Drinker Biddle & Reath LLP

(57) ABSTRACT

A Rotigotine-containing composition having a matrix mixture system formed from a polyvinylpyrrolidone and a combination of an acrylic pressure-sensitive adhesive with a silicone pressure-sensitive adhesive. The polyvinylpyrrolidone may be present in an amount of about 1-10% by weight in matrix mixture system. The acrylic pressure-sensitive adhesive may be present in an amount of about 1-25% by weight in the matrix mixture system. The silicone pressure-sensitive adhesive may be present in an amount of about 65-98% by weight in the matrix mixture system. The composition further includes 1-40% of Rotigotine on the basis of the total weight of the composition. The composition provides improved properties in the solubility, release and initial penetration level of Rotigotine. Also disclosed is a transdermal patch that includes the Rotigotine-containing composition, as well as methods of manufacturing and using the Rotigotine-containing composition.

12 Claims, 1 Drawing Sheet

(56) References Cited

U.S. PATENT DOCUMENTS

| | | |
|---|---|---|
| 2005/0033065 A1 | 2/2005 | Mueller et al. |
| 2005/0175678 A1 | 8/2005 | Breitenbach |
| 2005/0260254 A1* | 11/2005 | Breitenbach et al. ......... 424/449 |
| 2006/0216336 A1* | 9/2006 | Wolff ............................ 424/448 |

FOREIGN PATENT DOCUMENTS

| | | |
|---|---|---|
| CN | 1731995 | 2/2006 |
| CN | 101147739 | 3/2008 |
| WO | WO95-18603 A1 | 7/1995 |
| WO | WO-99/49852 A1 | 10/1999 |
| WO | WO9949852 A1 | 10/1999 |
| WO | WO-01/52823 A2 | 7/2001 |
| WO | WO0152823 | 7/2001 |
| WO | WO 02089778 A2 | 11/2002 |
| WO | WO02-102390 A1 | 12/2002 |
| WO | WO2005063237 A1 | 7/2005 |

OTHER PUBLICATIONS

Supplementary European Search Report for EP Application No. EP 08 77 3014, issued Nov. 4, 2013,.

J.D. Belluzzi, et al., N-0923, a Selective Dopamine D2 Receptor Agonist, is Efficacious in Rat and Monkey Models of Parkinson's Disease, Movement Disorders, vol. 9, No. 2, 1994, pp. 147-154 © Movement Disorder Society, 8 pages.

Jenner, Peter, DSc, FRPharmS, A Novel Dopamine Agonist for the Transdermal Treatment of Parkinson's Disease, Jul. 2005 Neurology 65(Suppl 1), 3 pages.

The Parkinson Study Group, A Controlled Trial of Rotigotine Monotherapy in Early Parkinson's Disease, © 2003 American Medical Association, (reprinted) Arch Neurology/vol. 60, Dec. 2003, www.archneurol.com, 8 pages.

PCT International Search Report for PCT/CN2008/001267, Oct. 30, 2008, 4 pages.

\* cited by examiner

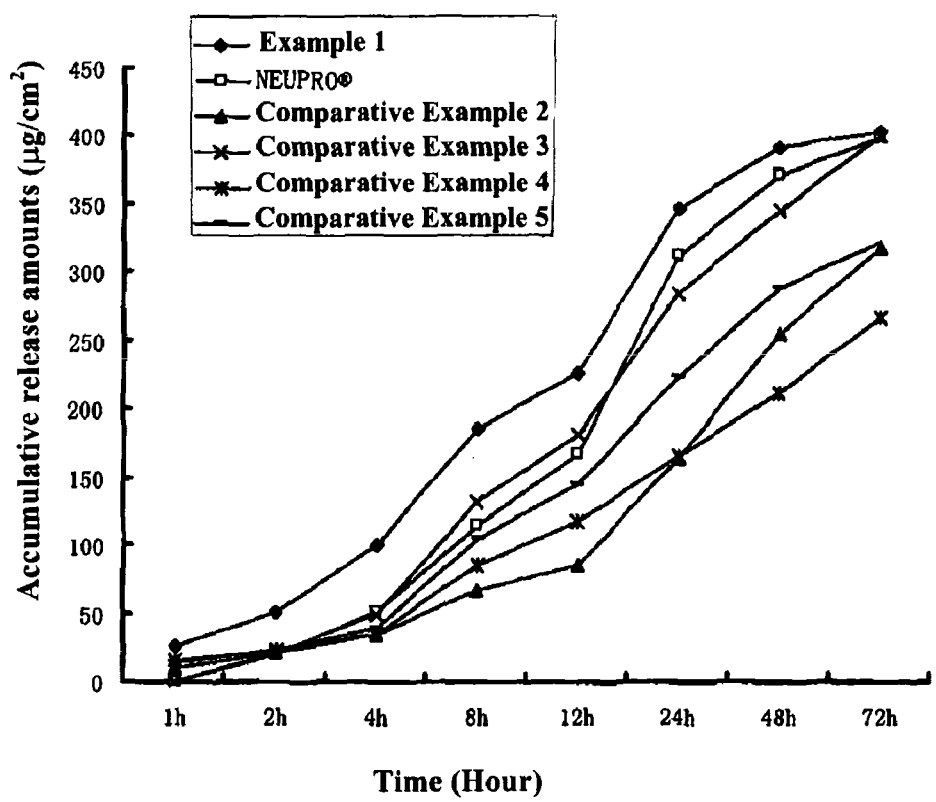

TRANSDERMAL PATCH CONTAINING ROTIGOTINE

TECHNICAL FIELD

The present invention relates to a composition containing Rotigotine and the use thereof in the manufacture of a Rotigotine-containing transdermal patch, wherein said composition is based on a matrix mixture system formed from a combination of an acrylic pressure-sensitive adhesive with a silicone pressure-sensitive adhesive, and polyvinylpyrrolidone which are present in a particular weight ratio. The present invention further relates to an improved transdermal patch containing Rotigotine comprising said composition. Said patch has improved properties in the solubility, release and initial penetration level of Rotigotine.

BACKGROUND ART

Rotigotine is a Non-Dihydroergotoxine $D_3/D_2/D_1$ dopamine receptor agonist, and long-term research shows that it has therapeutic effects on a variety of central nervous system diseases and mental disorders. As currently known, Rotigotine has superior effects in regard to the treatment or mitigation of Parkinson's disease, Restless Legs Syndrome, schizophrenia, depression and the like, and to the preventive treatment of Parkinson's disease (WO2005/063237). In particular, the therapeutic and mitigative effects of Rotigotine on Parkinson's disease are supported by substantive animal model studies and clinical tests (Neurology, Vol. 65 Suppl1: S3-S5/movement disorders Vol. 9 No. 2 P147-154; ARCH NEUROL, Vol. 60, December 2003: 1721-28). Rotigotine was first formulated into oral formulations, but was then found to exhibit an overly high clearance and a relatively short duration of action after oral intake. Thus, it could hardly achieve a therapeutically effective plasma concentration or be practically used owing to the need for frequent drug administration (Neurology, Vol. 65 Suppl1: S3-S5). Consequently, people tried to formulate Rotigotine into transdermal patches.

WO99/49852 describes a transdermal drug delivery system comprising Rotigotine on the basis of an acrylate or silicone. The adhesive used in this system is an acrylate or silicone, which independently of the other, forms a system involving a single adhesive together with the active drug. The system comprising an acrylate as adhesive has a low drug release rate; the system comprising a silicone as adhesive has a small drug load and a relatively low initial drug release rate.

WO2002/089778 describes the use of a silicone-based transdermal therapeutic system in the manufacture of an anti-Parkinson's disease medicament. This transdermal therapeutic system comprises Rotigotine as active ingredient. However, said system has a low drug release rate, and particularly requires too long a period of time to achieve an effective dosage. Consequently, there exist the following two problems: 1. the transdermal patch has to be changed frequently, for example once per 24 hours or shorter, to achieve an effective plasma concentration, and this is contrary to the advantage of convenient use of the patch by a patient; 2. the transdermal patch has a relatively low initial penetration level such that it takes too long a period of time for the drug to take effect after the application of the patch, usually resulting in the delay of the control of a patient's state of illness.

The inventors have thoroughly investigated the inherent disadvantages of the existing Rotigotine transdermal delivery systems. After a lot of tests, the inventors have found out that a matrix mixture system formed from a combination of an acrylic pressure-sensitive adhesive with a silicone pressure-sensitive adhesive, and polyvinylpyrrolidone which are present in a particular weight ratio is capable of sufficiently dissolving and releasing an effective amount of Rotigotine and of increasing the initial penetration level of Rotigotine. Thus, the Rotigotine releasing properties of the transdermal delivery system are improved. The present invention is hence finished.

CONTENTS OF THE INVENTION

The present invention provides a composition containing Rotigotine, which comprises, on the basis of the weight of the composition, 60-99%, preferably 70-95%, more preferably 75-90%, particularly preferably 79-84% by weight, of a matrix mixture system and 1-40% by weight of Rotigotine, wherein the said matrix mixture system is formed from a combination of an acrylic pressure-sensitive adhesive with a silicone pressure-sensitive adhesive, and polyvinylpyrrolidone which are present in a particular weight ratio, wherein:
 (1) the acrylic pressure-sensitive adhesive is present in an amount of about 1-25% by weight in the matrix mixture system,
 (2) the silicone pressure-sensitive adhesive is present in an amount of about 65-98% by weight in the matrix mixture system, and
 (3) the polyvinylpyrrolidone is present in an amount of about 1-10% by weight in the matrix mixture system.

In another aspect, the present invention provides the use of said composition containing Rotigotine in the manufacture of a transdermal patch.

Further still in another aspect, the present invention provides a transdermal patch containing Rotigotine, with a characteristic that the drug-containing matrix layer of the patch is based on a matrix mixture system formed from a combination of an acrylic pressure-sensitive adhesive with a silicone pressure-sensitive adhesive, and polyvinylpyrrolidone which are present in a particular weight ratio, wherein:
 (1) the acrylic pressure-sensitive adhesive is present in an amount of about 1-25% by weight in the matrix mixture system,
 (2) the silicone pressure-sensitive adhesive is present in an amount of about 65-98% by weight in the matrix mixture system, and
 (3) the polyvinylpyrrolidone is present in an amount of about 1-10% by weight in the matrix mixture system, and
the drug-containing matrix layer comprises 1-40% of Rotigotine on the basis of the total weight of the drug-containing matrix layer.

In one embodiment, the Rotigotine-containing transdermal patch of the present invention has a multi-layer complex structure comprising a backing layer, a drug-containing matrix layer comprising the active ingredient Rotigotine and a covering layer on the drug-containing matrix layer, with a characteristic that the drug-containing matrix layer is based on a matrix mixture system formed from a combination of an acrylic pressure-sensitive adhesive with a silicone pressure-sensitive adhesive, and polyvinylpyrrolidone which are present in a particular weight ratio, wherein:
 (1) the acrylic pressure-sensitive adhesive is present in an amount of about 1-25% by weight in the matrix mixture system,
 (2) the silicone pressure-sensitive adhesive is present in an amount of about 65-98% by weight in the matrix mixture system, and (3) the polyvinylpyrrolidone is present in an amount of about 1-10% by weight in the matrix mixture system, and the drug-containing matrix layer comprises 1-40% of Rotigotine on the basis of the total weight of the drug-containing matrix layer.

In the Rotigotine-containing composition of the present invention, the acrylic pressure-sensitive adhesive is present in an amount of preferably about 3-22%, more preferably about 4-20%, particularly preferably about 5-19%, especially preferably about 6-12.5%, by weight in the matrix mixture system.

In the Rotigotine-containing composition of the present invention, the silicone pressure-sensitive adhesive is present in an amount of preferably about 70-96%, more preferably about 75-95%, particularly preferably about 79-94%, especially preferably about 86.5-93%, by weight in the matrix mixture system.

In the Rotigotine-containing composition of the present invention, the polyvinylpyrrolidone is present in an amount of preferably about 1-8%, more preferably about 1-5%, particularly preferably about 1-2%, especially preferably about 1-1.5%, by weight in the matrix mixture system.

In the Rotigotine-containing composition of the present invention, Rotigotine is present in an amount of preferably about 3-20%, more preferably about 5-15%, particularly preferably about 8-11%, on the basis of the total weight of the composition.

The Rotigotine-containing composition of the present invention may further optionally comprise auxiliaries commonly used in transdermal drug delivery systems, such as permeation enhancers and antioxidants.

The Rotigotine-containing composition of the present invention preferably comprises a permeation enhancer, which may be present in an amount of about 0-15%, preferably about 2-13%, more preferably about 5-11%, particularly preferably 8-10% on the basis of the total weight of the composition.

The Rotigotine-containing composition of the present invention may comprise an antioxidant, which may be present in an amount of about 0-0.1% on the basis of the total weight of the composition.

In a preferred embodiment of the composition according to the present invention, the composition comprises, on the basis of the total weight of the composition, about 70-95%, preferably about 75-90%, of the matrix mixture system, wherein the acrylic pressure-sensitive adhesive is present in an amount of about 3-22%, preferably about 4-20%, by weight in the matrix mixture system, the silicone pressure-sensitive adhesive is present in an amount of about 70-96%, preferably about 75-95%, by weight in the matrix mixture system, and the polyvinylpyrrolidone is present in an amount of about 1-8%, preferably about 1-5%, by weight in the matrix mixture system; and comprises, on the basis of the total weight of the composition, about 3-20%, preferably about 5-15% by weight of Rotigotine and about 0-15%, preferably about 2-13% by weight of a permeation enhancer.

In a more preferred embodiment of the composition according to the present invention, the composition comprises, on the basis of the total weight of the composition, about 75-90%, particularly about 79-84%, of the matrix mixture system, wherein the acrylic pressure-sensitive adhesive is present in an amount of about 5-19%, particularly about 6-12.5%, by weight in the matrix mixture system, the silicone pressure-sensitive adhesive is present in an amount of about 79-94%, particularly about 86.5-93%, by weight in the matrix mixture system, and the polyvinylpyrrolidone is present in an amount of about 1-2%, particularly about 1-1.5%, by weight in the matrix mixture system; and comprises, on the basis of the total weight of the composition, about 5-15%, particularly about 8-11% of Rotigotine; and about 5-11%, particularly about 8-10% of a permeation enhancer.

The term "an acrylic pressure-sensitive adhesive" according to the present invention refers to an acrylic pressure-sensitive polymer and combinations thereof with a Eudragit-type acrylic resin.

The term "an acrylic pressure-sensitive polymer" as used herein, refers to a type of polymers known in the art. Such a type of polymers is formed by copolymerization of acrylic acids and derivatives thereof, and has a saturated hydrocarbon backbone and an ester side chain. A sticky acrylic pressure-sensitive polymer is obtainable by modifying the co-monomers and side chain groups. The monomers commonly used include soft monomers such as ethyl acrylate, 2-ethylhexyl acrylate or isooctyl acrylate, butyl acrylate and the like, for improving the adhesion of the pressure-sensitive polymers, hard monomers such as vinyl acetate, methyl acrylate, styrene, acrylonitrile, $C_{1-10}$ alkyl methacrylate, e.g., methyl methacrylate, ethyl methacrylate and n-butyl methacrylate and the like, for improving the cohesion of the pressure-sensitive polymers, and functional monomers such as (meth) acrylic acid, (meth)acrylamide, β-hydroxyethyl (meth)acrylate, β-hydroxypropyl (meth)acrylate, glycidyl (meth) acrylate, N-hydroxylmethylacrylamide, divinylbenzene, maleic acid, maleic anhydride and the like (YANG Yukun, Pressure-Sensitive Adhesives, Science Press, June 1994, p. 149-150), for forming chemical cross-links. The acrylic pressure-sensitive polymers used in the present invention are those particularly preferably copolymerized from butyl acrylate, isooctyl acrylate, vinyl acetate, acrylamide and α-methacrylic acid monomers. In particular, for example, the copolymer (A) of Example 2 in Table 1 on page 21 of CN1640500A (Beijing Kangbeide Pharmaceuticals Co., Ltd), which is incorporated herein in its entirety by reference, i.e. PAS-10-K, is copolymerized from 33.1% of butyl acrylate, 40.9% of isooctyl acrylate, 21.0% of vinyl acetate, 3.8% of acrylamide and 1.2% of α-methacrylic acid.

The term "a Eudragit-type acrylic resin", as used herein refers to, but not limited to, Eudragit® L100, Eudragit® S100, Eudragit® RL100, Eudragit® RS100, Eudragit® E100, Eudragit® L100-55, Eudragit® E PO, Eudragit® RL PO, Eudragit® RS PO and the like produced by Röhm Co. Ltd. (Germany), and Eudragit Nos. I, II, III and IV produced by Jiangsu Lianyun'gang Iodine Factory.

In the present invention, the acrylic pressure-sensitive adhesive is preferably a mixture of an acrylic pressure-sensitive polymer with a Eudragit-type acrylic resin, more preferably the acrylic-based adhesive composition disclosed in CN1640500A (Beijing Kangbeide Pharmaceuticals Co., Ltd), which consists of an acrylic pressure-sensitive polymer and Eudragit® E100 (see the adhesive composition used in CN1640500A, page 24, Table 4, Example 4), i.e. an adhesive composition consisting of PAS-10-K and different percents of Eudragit® E100, and particularly preferably an adhesive composition with a PAS-10-K to Eudragit® E100 ratio of 9:1.

The silicone pressure-sensitive adhesives according to the present invention are a type of pressure-sensitive adhesives prepared by dissolving low-viscosity dimethyl silicone polymers (12,000 to 15,000 cp) and silicone resins together in a suitable organic solvent. The ratio of resin to polymer and the silanol group content are important parameters for the determination of the properties of the silicone pressure-sensitive adhesives (Sobieski, et al., "Silicone Pressure Sensitive Adhesives," Handbook of Pressure Sensitive Technology, 2nd ed., 508-517, Van Nostrand Reinhold, New York (1989)). In the present invention, the silicone pressure-sensitive adhesives are preferably commercially available, including the BIO-PSA® 4600 series, BIO-PSA® 4500 series, BIO-PSA® 4400 series, BIO-PSA® 4300 series, BIO-PSA® 4200 series and BIO-PSA® 4100 series silicone pressure-sensitive adhesives sold by Dow Corning Corporation. Anti-amine silicone pressure-sensitive adhesives of the BIO-PSA® 4300 series and BIO-PSA® 4200 series are more preferred.

The polyvinylpyrrolidone used in the present invention is useful as a crystallization inhibitor in transdermal drug delivery formulations. Polyvinylpyrrolidones or "PVPs" are non-ionic water-soluble macromolecular compounds formed by polymerization of N-vinylpyrrolidone under certain conditions. The use of polyvinylpyrrolidones in transdermal drug delivery formulations is already mentioned in EP0524776. Suitable PVPs include the products under the trademark Kollidon produced by BASF. In the present invention, Kollidon 17PF, 25, 30 and 90 are preferably used, and Kollidon 30 and Kollidon 90 are particularly preferred.

The inventors have found out, after conducting a lot of tests, that a matrix mixture system comprising a combination of an acrylic pressure-sensitive adhesive with a silicone pressure-sensitive adhesive in a certain ratio improves the solubility and skin permeability of the drug significantly, and the addition of a small amount of polyvinylpyrrolidone further improves the drug load and penetration level without affecting the mechanical properties of the patch. Although an increased percent by weight of the acrylic pressure-sensitive adhesive in the matrix mixture system increases the solubility and initial dispersion rate of the drug, it lowers the drug's sustained release ability in the system, and finally results in a relatively high level of drug residue after the application of the patch. A decreased percent by weight of the acrylic pressure-sensitive adhesive in the matrix mixture system fails to increase the initial dispersion rate of the drug. Thus, the ratio of the acrylic pressure-sensitive adhesive to the silicone pressure-sensitive adhesive is within a limited range. The polyvinylpyrrolidone is a solubility enhancer and crystallization inhibitor. Anyone with ordinary skill in the art can determine its suitable amount by conducting conventional tests. In the system, an excessively high polyvinylpyrrolidone content will affect the mechanical properties of the patch, and a suitable amount of polyvinylpyrrolidone can change the dispersion state of the drug in the system.

In the transdermal patch containing Rotigotine of the present invention, the acrylic pressure-sensitive adhesive is present in an amount of about 1-25%, preferably about 3-22%, more preferably about 4-20%, particularly preferably about 5-19%, especially preferably about 6-12.5%, by weight in the matrix mixture system.

In the transdermal patch containing Rotigotine of the present invention, the silicone pressure-sensitive adhesive is present in an amount of about 65-98%, preferably about 70-96%, more preferably about 75-95%, particularly preferably about 79-94%, especially preferably about 86.5-93%, by weight in the matrix mixture system.

In the transdermal patch containing Rotigotine of the present invention, the polyvinylpyrrolidone is present in an amount of about 1-10%, preferably about 1-8%, more preferably about 1-5%, particularly preferably about 1-2%, especially preferably about 1-1.5%, by weight in the matrix mixture system.

In the transdermal patch containing Rotigotine of the present invention, the Rotigotine is present in an amount of about 1-40%, preferably about 3-20%, more preferably about 5-15%, particularly preferably about 8-11%, on the basis of the total weight of the drug-containing matrix layer.

In the transdermal patch containing Rotigotine of the present invention, the matrix mixture system is present in an amount of 60-99%, preferably 70-95%, more preferably 75-90%, particularly preferably 79-84%, on the basis of the total weight of the drug-containing matrix layer.

In the transdermal patch of the present invention, the drug-containing matrix layer may optionally comprise auxiliaries commonly used in transdermal drug delivery systems, such as permeation enhancers, antioxidants and so on, so as to assist to improve the properties of the patch.

The transdermal patch of the present invention preferably comprises a permeation enhancer, which may be present in an amount of about 0-15%, preferably about 2-13%, more preferably about 5-11%, particularly preferably 8-10% on the basis of the total weight of the drug-containing matrix layer.

The transdermal patch of the present invention may comprise an antioxidant, which may be present in an amount of about 0-0.1% on the basis of the total weight of the drug-containing matrix layer.

In a preferred embodiment of the transdermal patch according to the present invention, the drug-containing matrix layer of the transdermal patch comprises, on the basis of the total weight of the drug-containing matrix layer, about 70-95%, preferably about 75-90%, of the matrix mixture system, wherein the acrylic pressure-sensitive adhesive is present in an amount of about 3-22%, preferably about 4-20%, by weight in the matrix mixture system, the silicone pressure-sensitive adhesive is present in an amount of about 70-96%, preferably about 75-95%, by weight in the matrix mixture system, and the polyvinylpyrrolidone is present in an amount of about 1-8%, preferably about 1-5%, by weight in the matrix mixture system; and comprises, on the basis of the total weight of the drug-containing matrix layer, about 3-20%, preferably about 5-15% of Rotigotine; and about 0-15%, preferably about 2-13% of a permeation enhancer.

In a more preferred embodiment of the transdermal patch according to the present invention, the drug-containing matrix layer of the transdermal patch comprises, on the basis of the total weight of the drug-containing matrix layer, about 75-90%, particularly about 79-84%, of the matrix mixture system, wherein the acrylic pressure-sensitive adhesive is present in an amount of about 5-19%, particularly about 6-12.5%, by weight in the matrix mixture system, the silicone pressure-sensitive adhesive is present in an amount of about 79-94%, particularly about 86.5-93%, by weight in the matrix mixture system, and the polyvinylpyrrolidone is present in an amount of about 1-2%, particularly about 1-1.5%, by weight in the matrix mixture system; and comprises, on the basis of the total weight of the drug-containing matrix layer, about 5-15%, particularly about 8-11% of Rotigotine; and about 5-11%, particularly about 8-10% of a permeation enhancer.

Permeation enhancers useful in the present invention may be selected from the group consisting of (1) surfactants, such as tweens, spans, sodium lauryl sulfate, sodium dodecylsulfate and the like, (2) organic solvents including alcohols, polyols, esters, dimethyl sulfoxide and analogues thereof, specific examples may be mentioned, such as ethyl acetate, propylene glycol diacetate, glycol, glycerine, dimethyl sulfoxide, decylmethyl sulfoxide etc., (3) fatty acids, fatty alcohols and fatty acid esters, such as oleic acid, lactic acid, myristic acid, lauryl acid, isopropyl myristate and the like, (4) azones and pyrrolidone derivatives, such as N-methylpyrrolidone, 1,5-dimethylpyrrolidone, 5-carboxylpyrrolidone and the like, (5) keratinous emollients and softeners, such as salicylic acid and urea, and (6) terpenes, such as menthol, camphor and the like. Isopropyl myristate, lauryl acid and N-methylpyrrolidone are preferred.

A variety of antioxidants are suitable for use in the present invention. For example, suitable antioxidants may be selected from inorganic and organic antioxidants and determined by conventional stability tests in the art. Said antioxidants may be selected from, for example, the group consisting of vitamin E, ascorbyl palmitate, sodium metasulfite or mixtures thereof. Vitamin E and ascorbyl palmitate are preferred.

The active ingredient, Rotigotine used in the present invention may be a free base of Rotigotine or a pharmaceutically acceptable salt of Rotigotine, such as a hydrochloride, sulfate, nitrate or succinate of Rotigotine, but a free base of Rotigotine is preferred.

In the transdermal patch of the present invention, the backing layer is made from a backing material well known by those with skill in the art; such a backing material may be aluminum foil, polyethylene glycol terephthalate, polyethylene or non-woven fabric. In the transdermal patch of the present invention, the covering layer applied on the drug-containing matrix layer is made from a protective material well known by those with skill in the art; such a protective material may be a polyester, polyvinyl chloride or polyethylene glycol terephthalate film, or the above-mentioned film is treated conventionally with a release coating, including the application of a silicone resin or fluorine resin on the surface of the film in direct contact with the drug-containing matrix layer. The covering layer of the transdermal patch of the present invention is preferably the polyester film surface coated with a fluorine resin.

The transdermal patch of the present invention may be processed into various shapes and sizes in regard to practical needs, and its surface area is preferably 1.0-150 $cm^2$ with preferred specifications of 4.5 mg Rotigotine/10 $cm^2$, 9 mg Rotigotine/20 $cm^2$, 13.5 mg Rotigotine/30 $cm^2$, and 18 mg Rotigotine/40 $cm^2$.

The drug-containing matrix layer of the Rotigotine-containing transdermal patch of the present invention has a thickness of 20-80 µm, preferably 40-60 µm.

The drug-containing matrix layer of the Rotigotine-containing transdermal patch of the present invention may be in the form of a mono-layer or multi-layer complex well-known in the art. Such transdermal patch structure may comprise a backing layer, a high-content active drug Rotigotine layer and/or an intermediate-content active drug Rotigotine layer, a low-content active drug Rotigotine layer, and a covering layer.

The Rotigotine-containing composition of the present invention can be prepared by techniques known in the art. For example, in accordance with the formula, polyvinylpyrrolidone is weighed into a suitable container, a suitable amount of the solution of an antioxidant (if present) in ethanol is added, and the polyvinylpyrrolidone is dissolved by stirring. Into the same container, Rotigotine, a silicone pressure-sensitive adhesive, an acrylic pressure-sensitive adhesive (wherein the acrylic pressure-sensitive polymer is prepared according to the process for preparing a (meth)acrylate copolymer comprising (meth)acrylamide or an N,N-substituted monomer thereof as described in the Example on pages 20-21 of CN1640500A) and an optional permeation enhancer are added according to the formula, a suitable amount of a solvent, such as ethyl acetate, is added, and the components are sufficiently dissolved by stirring. At last, the polyvinylpyrrolidone is completely dissolved by adding a suitable amount of ethanol and performing ultrasonic treatment for 30 minutes, and a Rotigotine-containing composition is thus prepared.

The transdermal patch of the present invention may be prepared by techniques known in the art. The techniques comprise for example, the following steps:

1. Adding into a suitable container, polyvinylpyrrolidone according to the formula, a suitable amount of a solution of an antioxidant (if present) in ethanol and stirring to dissolve the polyvinylpyrrolidone;

2. Adding into the same container, Rotigotine, a silicone pressure-sensitive adhesive, an acrylic pressure-sensitive adhesive (wherein the acrylic pressure-sensitive polymer is prepared according to the process for preparing a (meth)acrylate copolymer comprising (meth)acrylamide or an N,N-substituted monomer thereof as described in the Example on pages 20-21 of CN1640500A) and an optional permeation enhancer according to the formula, a suitable amount of a solvent such as ethyl acetate to build up the volume to a certain level, and stirring to sufficiently dissolve the components;

3. Adding a suitable amount of ethanol and performing ultrasonic treatment for 30 minutes to completely dissolve the polyvinylpyrrolidone, at which point the resultant mixture becomes clear and transparent, hence obtaining the material for the drug-containing matrix layer of the transdermal patch;

4. Finally, applying the resulting material with a certain thickness on a patulous backing material, primarily drying it by air, then moving it to an oven where it is dried for 2 hours at 80° C., removing the volatile solvent prior to taking it out and cooling it, later applying it with a covering layer, and finally die-cutting it to patches with certain surface areas and shapes.

The transdermal patch of the present invention comprising a drug-containing matrix layer in the form of a multi-layer complex may be prepared according to a conventional process known in the art. For example, first of all, matrices comprising the same concentration or different concentrations of the active drug are formulated. Then the matrices are respectively applied to a backing support material and a specially made, protective liner by a scraper method and dried to take shape. Subsequently, the matrix layer applied on the protective liner is transferred onto the matrix layer applied on the backing support material, the protective liner is removed, the layers are transferred one by one according to this method and laminated, then a covering layer is applied onto the laminate, and finally patches comprising a drug-containing matrix layer in the form of multi-layer complex are die-cut into certain surface areas and shapes (see LIANG Bingwen, Transdermal Drug Delivery Formulations, China Medical—Pharmaceutical Science and Technology Publishing House, September 1992, p. 329-334).

The present invention provides a transdermal patch containing Rotigotine which can sufficiently dissolve and release an effective amount of drug, Rotigotine. This patch has an increased Rotigotine initial penetration level. Judging from this feature, it can be predicted that the transdermal patch containing Rotigotine of the present invention needs a relatively short period of time to take effect in clinical use.

DESCRIPTION OF THE DRAWING

FIG. 1 shows the curve of the in vitro transdermal release amount (µg/$cm^2$) accumulated from 1 to 72 hours of Rotigotine in the transdermal patches of Example 1 (the present invention), NEUPRO® (Comparative Example 1) and Comparative Examples 2-5.

EXAMPLES

The present invention is further illustrated by, but not limited to, the following Examples.

Preparation of a Transdermal Patch

Example 1

Into a suitable container, 0.05 g of polyvinylpyrrolidone (Kollidon 30 produced by BASF Germany) was added, 1 ml of a solution of ascorbyl palmitate (produced by Beijing Chen Ao Hi-Tech Co. Ltd.) in ethanol (3 mg/ml) as antioxidant was added, and the polyvinylpyrrolidone was dissolved by stirring. Into the same container, 0.45 g of a Rotigotine base (which was synthesized and prepared according to the process described in "Synthesis and radioreceptor binding activity of N-0437, a new, extremely potent and selective D2 dopamine receptor agonist", Pharm Weekbl Sci, Vol. 7.1985: 208-211), 6.25 g of a 30% solid content silicone pressure-sensitive adhesive (BIO-PSA® 7-4302 Dow Corning Corporation), 0.72 g of a 35% solid content acrylic pressure-sensitive adhesive (which was prepared according to the process for preparing a (meth)acrylate copolymer comprising (meth)acrylamide or an N,N-substituted monomer thereof as described in the Example on pages 20-21 of CN1640500A, wherein the monomer used in Example 2 was used for the preparation of an acrylic pressure-sensitive polymer, and the acrylic pressure-sensitive polymer thus prepared was mixed with Eudragit® E100 (produced by Röhm Germany) in a ratio of 9:1 (dry weight)) and 0.5 g of isopropyl myristate (Jiangsu Kunshan Huaxin Daily Chemicals Co., Ltd) was added. A suitable amount of ethyl acetate (produced by Beijing Organic Chemical Plant, chemically pure) was added to build up the volume to a certain level, and the components were sufficiently mixed by stirring. Subsequently, a suitable amount of ethanol (produced by Beijing Yili Fine Chemical Co., Ltd., chemically pure) was added, and ultrasonic treatment was performed for 30 minutes to completely dissolve the polyvinylpyrrolidone to form a mucilage. At that time, the mucilage was clear and transparent. The resulting mucilage was applied with a certain thickness to a backing material of a patulous polyester film (SCOTCHPAK® 1109) to prepare a drug-containing matrix layer, and then dried at 85° C. for 2 to 3 hours to obtain a thickness of about 40 μm. A fluorine-containing layer-coated polyester film (SCOTCHPAK® 1022) was then applied on the resulting drug-containing matrix layer, and finally the resultant layers were die-cut to produce patches having certain surface areas and sizes, i.e. the transdermal patches of the present invention. The patches contained 0.45 mg/cm$^2$ of Rotigotine and the amounts (parts by weight) of the other components as shown in Table 1.

Examples 2 to 3

Patches of Examples 2 and 3 were prepared according to the process described in Example 1 wherein the components of the drug-containing matrix layer and the amounts thereof (parts by weight) were as shown in Table 1.

Examples 4 to 8

Patches of Examples 4-8 were prepared according to the process described in Example 1, wherein the components of the drug-containing matrix layer and the amounts thereof (parts by weight) were as shown in Table 2.

Comparative Example 1

A commercially available Rotigotine patch NEUPRO® was obtained from Schwarz Pharm AG. with a Rotigotine content of 0.45 mg/cm$^2$

Comparative Examples 2 to 5

Patches prepared according to the process described in Example 1: the formula of Comparative Example 2 contained no silicone pressure-sensitive adhesives, the formula of Comparative Example 3 contained no acrylic pressure-sensitive adhesive, the formula of Comparative Example 4 contained no polyvinylpyrrolidone (the process for the preparation of the patch of Comparative Example 4 did not have the step of dissolving polyvinylpyrrolidone), and the amounts of the acrylic and silicone pressure-sensitive adhesives in the formula of Comparative Example 5 were beyond the ranges of the present invention. The specific formulae of the drug-containing matrix layers of these patches are as shown in Table 1.

Measurement of the Release Amount of Rotigotine in the Transdermal Patches

The above-mentioned patches were subjected to in vitro transdermal tests according to the experimental methods introduced by the Transdermal Drug Delivery Formulations (LIANG Bingwen, China Medical—Pharmaceutical Science and Technology Publishing House, September 1992, p. 252).
Experimental Apparatus: FRANZ-type transdermal diffuser (Model: TK-60B, Shanghai Kaikai Technology&Trade Co., Ltd.)
Experimental Carrier: freshly prepared whole-thickness skin from the rib part and back of a guinea pig (prepared according to the Transdermal Drug Delivery Formulations, LIANG Bingwen, China Medical—Pharmaceutical Science and Technology Publishing House, September 1992, p. 252)
Number of Samples: 5 (five samples for each tested subject of the patches of the Examples or Comparative Examples)
Patch Surface Area: 10 cm$^2$
Diffusion Medium: a phosphate buffer of pH 6.2
Measuring Method: high-performance liquid chromatography (UV detector, Waters, Model: 2487)

The 1-72 hours accumulative release amounts (μg/cm$^2$) of Rotigotine in the patches of Example 1 and Comparative Examples 1-5 were measured, and the results are as shown in FIG. 1. The 0-12 hours accumulative release amounts (μg/cm$^2$) of Rotigotine in the patches of Examples 1-3 and Comparative Examples 2-5 are as shown in Table 1.

TABLE 1

| | Drug-containing matrix layer | | | | | | |
|---|---|---|---|---|---|---|---|
| | Example 1 | Example 2 | Example 3 | Comparative Example 2 | Comparative Example 3 | Comparative Example 4 | Comparative Example 5 |
| | | | | Parts by weight | | | |
| Acrylic pressure-sensitive adhesive | 5 | 10 | 15 | 80 | — | 5 | 50 |

TABLE 1-continued

| | Drug-containing matrix layer | | | | | | |
|---|---|---|---|---|---|---|---|
| | Example 1 | Example 2 | Example 3 | Comparative Example 2 | Comparative Example 3 | Comparative Example 4 | Comparative Example 5 |
| | | | | Parts by weight | | | |
| Silicone pressure-sensitive adhesive (BIO-PSA ® 7-4302) | 75 | 70 | 65 | — | 80 | 75 | 30 |
| Polyvinylpyrrolidone (Kollidon 30) | 1 | 1 | 1 | 1 | 1 | — | 1 |
| Rotigotine base | 9 | 9 | 9 | 9 | 9 | 9 | 9 |
| Isopropyl myristate | 10 | 10 | 10 | 10 | 10 | 11 | 10 |
| Ascorbyl palmitate | 0.0006 | 0.0006 | 0.0006 | 0.0006 | 0.0006 | 0.0006 | 0.0006 |
| 0-12 hours accumulative release amounts (μg/cm$^2$) of Rotigotine | 226.7 | 221.4 | 210.3 | 86.3 | 181.4 | 117.7 | 144.7 |

Note:
All the Examples and Comparative Examples (including the test sample of NEUPRO ® of Comparative Example 1) contain the same amount of Rotigotine (0.45 mg/cm$^2$) to ensure the comparability of the experimental results.

TABLE 2

| | Drug-containing Matrix layer | | | | |
|---|---|---|---|---|---|
| | Example 4 | Example 5 | Example 6 | Example 7 | Example 8 |
| | | | Parts by weight | | |
| Acrylic pressure-sensitive adhesive | 5 | 5 | 5 | 5 | 5 |
| Silicone pressure-sensitive adhesive (BIO-PSA ® 7-4302) | 93 | 84 | 70 | 65 | 65 |
| Polyvinylpyrrolidone (Kollidon 30) | 1 | 1 | 2 | 2 | 2 |
| Rotigotine base | 1 | 5 | 15 | 18 | 25 |
| Isopropyl myristate | 0 | 5 | 8 | 10 | 3 |
| Ascorbyl palmitate | 0.0006 | 0.0006 | 0.0006 | 0.0006 | 0.0006 |

It can be seen from FIG. 1 that Example 1 of the present invention had a higher transdermal release amount than NEUPRO® and the patches of the other Comparative Examples, and showed the characteristic of zero-order release. More importantly, it can be seen from FIG. 1 that the transdermal patches of the present invention had a significantly increased drug penetration level within the initial 12 hours of diffusion, which means that the patches took effect faster. It can be seen from FIG. 1 and Table 1 that the transdermal patches of the present invention exhibited unique advantages of Rotigotine transdermal rate over the patches of Comparative Examples 2-5, and had the properties of a longer duration and a uniform drug release.

The invention claimed is:

1. A rotigotine-containing transdermal patch comprising a matrix layer composition,
wherein the matrix layer composition comprises, on the basis of the total weight of the matrix layer composition, 79-84% by weight of a matrix mixture system and 8-11% by weight of rotigotine,
wherein the matrix mixture system is formed from a combination of a first adhesive comprising an acrylate copolymer with a second adhesive comprising dimethyl silicone polymers and silicone resins, and polyvinylpyrrolidone, wherein
(1) the first adhesive is present in an amount of 5-15% by weight in the matrix mixture system,
(2) the second adhesive is present in an amount of 65-75% by weight in the matrix mixture system, and
(3) the polyvinylpyrrolidone is present in an amount of 1-1.5% by weight in the matrix mixture system;
wherein the rotigotine is in the form of the free base or a pharmaceutically acceptable salt,
wherein the acrylate copolymer is copolymerized from monomer units selected from the group consisting of butyl acrylate, isooctyl acrylate, vinyl acetate, acrylamide, and α-methacrylic acid,
wherein the 0-12 hour accumulative release amount of rotigotine is about 210 to about 226 μg/cm$^2$,
wherein the matrix layer composition further comprises at least one auxiliary selected from the group consisting of permeation enhancers and antioxidants, and wherein if the permeation enhancer is present, the permeation enhancer is present in an amount of 8-10% based on the total weight of the matrix layer composition.

2. The rotigotine-containing transdermal patch of claim 1, wherein the permeation enhancer is selected from the group consisting of surfactants, alcohols, polyols, esters, dimethyl sulfoxide, fatty acids, fatty alcohols, fatty acid esters, azones, N methylpyrrolidone, 1,5-dimethylpyrrolidone, 5-carboxylpyrrolidone, salicylic acid, and terpenes.

3. The rotigotine-containing transdermal patch of claim 1, wherein the antioxidant is selected from the group consisting of vitamin E, ascorbyl palmitate, sodium metasulfite and mixtures thereof.

4. The rotigotine-containing transdermal patch of claim 1, wherein the permeation enhancer is selected from the group consisting of isopropyl myristate, lauryl acid and N-methylpyrrolidone.

5. The rotigotine-containing transdermal patch of claim 1, wherein the acrylate copolymer comprises butyl acrylate monomer units.

6. The rotigotine-containing transdermal patch of claim 1, wherein the acrylate copolymer comprises isooctyl acrylate monomer units.

7. The rotigotine-containing transdermal patch of claim 1, wherein the acrylate copolymer comprises vinyl acetate monomer units.

8. The rotigotine-containing transdermal patch of claim 1, wherein the acrylate copolymer comprises acrylamide monomer units.

9. The rotigotine-containing transdermal patch of claim 1, wherein the acrylate copolymer comprises α-methacrylic acid monomer units.

10. The rotigotine-containing transdermal patch of claim 1, wherein the acrylate copolymer comprises butyl acrylate, isooctyl acrylate, vinyl acetate, acrylamide, and α-methacrylic acid monomer units.

11. The rotigotine-containing transdermal patch of claim 1, wherein the second adhesive is a pressure-sensitive adhesive.

12. The rotigotine-containing transdermal patch of claim 1, wherein the matrix mixture system is saturated with rotigotine.

* * * * *